(12) United States Patent
Rao (10) Patent No.: US 8,395,777 B2
(45) Date of Patent: Mar. 12, 2013

(54) METHOD AND APPARATUS FOR TRACE GAS DETECTION USING INTEGRATED WAVELENGTH MODULATED SPECTRA ACROSS MULTIPLE LINES

(75) Inventor: Gottipaty Rao, West Hempstead, NY (US)

(73) Assignee: Adelphi University, Garden City, NY (US)

( * ) Notice: Subject to any disclaimer, the term of this patent is extended or adjusted under 35 U.S.C. 154(b) by 147 days.

(21) Appl. No.: 13/025,991

(22) Filed: Feb. 11, 2011

(65) Prior Publication Data

US 2012/0113426 A1    May 10, 2012

Related U.S. Application Data

(63) Continuation-in-part of application No. 12/878,553, filed on Sep. 9, 2010.

(51) Int. Cl.
*G01N 21/00* (2006.01)
(52) U.S. Cl. ...................................................... 356/437
(58) Field of Classification Search .................. None
See application file for complete search history.

(56) References Cited

U.S. PATENT DOCUMENTS

| | | |
|---|---|---|
| 4,434,490 A | 2/1984 | Kavaya et al. |
| 5,026,991 A | 6/1991 | Goldstein et al. |
| 5,331,409 A | 7/1994 | Thurtell et al. |
| 7,004,909 B1 | 2/2006 | Patel et al. |
| 7,102,751 B2 | 9/2006 | Harper |
| 2007/0064748 A1 | 3/2007 | Mirov et al. |
| 2007/0229834 A1 | 10/2007 | Patel et al. |
| 2010/0002234 A1* | 1/2010 | Cormier et al. ............... 356/436 |

FOREIGN PATENT DOCUMENTS

JP     2009-047677 A     3/2009

OTHER PUBLICATIONS

Karpf et al. "Enhanced Sensitivity for the Detection of Trace Gases Using Multiple Line Integrated Absorption Spectroscopy", *Applied Optics*, 2009, vol. 48, No. 2, pp. 5061-5066.
Karpf et al. "Enhancement of trace gas detection by integrating wavelength modulated spectra across multiple lines", *Applied Optics*, 2010, vol. 49, No. 8, pp. 1406-1414.
Karpf et al. "Absorption and wavelength modulation spectroscopy of $NO_2$ using a tunable, external cavity continuous wave quantum cascade laser", *Applied Optics*, 2009, vol. 48, No. 2, pp. 408-413.
International Search Report mailed Apr. 6, 2012 for the PCT Application No. PCT/US2011/045229.

(Continued)

*Primary Examiner* — Gregory J Toatley
*Assistant Examiner* — Juan D Valentin, II
(74) *Attorney, Agent, or Firm* — Leason Ellis LLP.

(57) ABSTRACT

An apparatus and technique are invented that enhance the sensitivity of a spectrometer for trace gas detection by employing wavelength modulation spectroscopy (WMS) and integrating the absolute value of the recorded spectra across multiple absorption lines (features) of the species. The sensitivity is further enhanced by conducting WMS with large modulation depths. This technique is implemented using a continuously tunable external cavity CW quantum cascade laser to record the second harmonic wavelength modulated spectra of $NO_2$ across the peak of the R-branch from 1629.5 $cm^{-1}$ to 1633.9 $cm^{-1}$. By integrating the absolute value of the resulting spectra, the detection sensitivity of $NO_2$ is improved by a factor of 40 compared to the sensitivity achieved using single line WMS with the same apparatus. A sensitivity of approximately 6 ppb can be obtained using a short-path cell (a 1 m absorption cell with 2 passes) which can be significantly improved using multipass cells and cavity enhanced techniques.

28 Claims, 8 Drawing Sheets

OTHER PUBLICATIONS

International Search Report mailed May 25, 2012 for the PCT Application No. PCT/US2012/022898.

International Search Report mailed May 29, 2012 for the PCT Application No. PCT/US2012/022900.

Kosterev et al., "Chemical sensing with pulsed QC-DFB lasers operating at 6.6 μm", *Appl. Phys. B.*, 2002 vol. 75, pp. 351-357.

Tittle at al., "Recent advancesin trace gas detection using quantum and interband cascade lasers", *Rev. of Laser Eng.*, 2006, vol. 34, pp. 275-282.

Kosterev et al., " Application of quantum cascade lasers to trace gas analysis", *App. Phys. B*, 2008, vol. 90, pp. 165-176.

Wysocki et al., "Widely tunable mode-hop free external cavity quantum cascade laser for high resolution spectroscopic applications", *App. Phys. B*, 2005, vol. 81, pp. 769-777.

Werle, "Review of recent advances in laser based gas monitors", *Spectrochimica Acta A*, 1998, vol. 54, pp. 197-236.

Rothman et al., "The HITRAN 2004 molecular spectroscopic database", *J. Quant. Spectrosc. Radiat. Transfer*, 2005, vol. 96, pp. 139-204.

Office Action dated Dec. 21, 2011 for the parent U.S. Appl. No. 12/878,553.

* cited by examiner

METHOD AND APPARATUS FOR TRACE GAS DETECTION USING INTEGRATED WAVELENGTH MODULATED SPECTRA ACROSS MULTIPLE LINES

CROSS REFERENCE TO RELATED APPLICATIONS

This application is a continuation-in-part of prior non-provisional application Ser. No. 12/878,553 filed Sep. 9, 2010 and its contents are incorporated herein by reference. This application is related to non-provisional application Ser. No. 13/026,011 filed on even date herewith.

BACKGROUND OF THE INVENTION

The present invention relates to the detection of trace gas species including explosives, with high sensitivity and specificity, and more particularly to tunable laser-based systems for trace detection of nitrogen dioxide.

The real-time monitoring of trace gas species is of great interest in a wide range of fields, including environmental science, safety monitoring and air quality control (e.g., for compliance with Environmental Protection Agency regulations), defense and homeland security (e.g., for the detection of trace amounts of explosives or explosive compounds), and non-invasive medical diagnostics (e.g., breath analysis). See for example, United States Environmental Protection Agency, "National Air Quality Status and Trends Through 2007, EPA-454/R-08-006", United States Environmental Protection Agency, Washington, D.C. (2008); J. Hildenbrand et al., "Explosive detection using infrared laser spectroscopy," *Proc. SPIE* 7222, 72220B-1-12 (2009); T. H. Risby, S. F. Solga, "Current status of clinical breath analysis," *Appl. Phys. B* 85, 421-426 (2006) and a presentation by the present inventor, Gottipaty N Rao and by A. Karpf, "Sensors at ppb Sensitivity or Better Based on Multiple Line Integration Spectroscopy Techniques," *Laser Applications to Chemical, Security and Environmental Analysis* (*LACSEA*) 2010 paper: LPDP2.

In these applications, the concentrations of the trace gas species typically range from parts per trillion ($10^{-12}$) to parts-per-million ($10^{-6}$) levels and thus require techniques that are both highly sensitive and selective. Nitrogen oxides ($NO_x$) are of particular interest since they are some of the most damaging of these pollutants. They play important roles in the formation of photochemical smog, the formation of tropospheric ozone, and the formation of acid rain, and thus can directly impact public health.

Laser-based techniques for trace gas detection have many advantages over other techniques because of their ability to provide real-time monitoring capabilities with greater sensitivity and selectivity. In particular, Quantum Cascade Lasers are attractive sources for trace gas detection because they operate in the mid-infrared region ($\lambda$=4 µm to 24 µm) and thus provide access to the fundamental rotational-vibrational transitions of molecular species. Examples may be found in A. A. Kosterev et al., "Chemical Sensing with pulsed QC-DFB lasers operating at 6.6 µm" *Appl. Phys. B.* 75, 351-357 (2002); F. K. Tittel et al., "Recent Advances in Trace Gas Detection Using Quantum and Interband Cascade Lasers," *Rev. of Laser Eng.* 34, 275-282 (2006); A. Kosterev et al., "Application of quantum cascade lasers to trace gas analysis," *Appl. Phys. B* 90, 165-176 (2008); R. F. Curl et. al., "Quantum cascade lasers in chemical physics," *Chem. Phys. Lett.* 487, 1-18 (2010); and a recent review article by the inventor, Gottipaty N Rao and by A. Karpf, "External cavity tunable quantum cascade lasers and their applications to trace gas monitoring," *Applied Optics*, Vol. 50 Issue 4, pp. A100-A115. (2011).

The quantum cascade lasers offer improved sensitivity of several orders of magnitude over near-infrared diode laser based techniques that employ the detection of the overtones of the molecular transitions. Quantum cascade lasers have been used to detect several trace gasses (e.g., CO, $CO_2$, NO, $NO_2$, $NH_3$, $CH_4$ and $N_2O$) with different spectroscopic techniques (e.g., Laser Absorption Spectroscopy, Cavity Ring-down Spectroscopy, Integrated Cavity Output Spectroscopy) as described in the review article by the present inventor Gottipaty N Rao and by Andreas Karpf. By employing an external cavity arrangement, a quantum cascade laser provides a narrow line width ($\Delta\nu$~0.001 $cm^{-1}$), highly stable and reproducible tunable continuous wave ("CW") output, and a wide continuous tuning range; all of which are essential for the study of complex spectra. The investigation of trace gas species involves just such a study of complex spectra. See G. Wysocki, et al., "Widely tunable mode-hop free external cavity quantum cascade laser for high resolution spectroscopic applications," *Appl. Phys. B* 81, 769-777 (2005) and articles by the present inventor, A. Karpf, G. N. Rao, "Absorption and wavelength modulation spectroscopy of $NO_2$ using a tunable, external cavity continuous wave quantum cascade laser," *Appl. Opt.* 48, 408-413 (2009); Gottipaty N Rao et al., "A Trace Gas Sensor at ppb Sensitivity Based on Multiple Line Integration Spectroscopy," *Conference on Lasers and Electro-Optics* (*CLEO*) 2010 paper: JWA60.

Laser absorption spectroscopy is based on recording the change in intensity of laser radiation as it passes through a region containing the sample of interest. As the laser is tuned across a transition, the transmitted laser intensity is a function of frequency $\nu$ given by Beer's law:

$$I(\nu)=I_0(\nu)e^{-\alpha(\nu)L} \quad (1)$$

where $I_0$ is the incident laser intensity, L is the optical path length, $\alpha(\nu)$ is the absorption coefficient at frequency $\nu$. In the low concentration regime (where $\alpha(\nu)L \leq 0.05$) one can approximate equation (1) as:

$$I(\nu)=I_0(\nu)[1-\alpha(\nu)L]. \quad (2)$$

When using laser absorption spectroscopy, the sensitivity of a spectrometer is often determined by taking the ratio of the amplitudes of the absorption line to that of the noise level.

The sensitivity of a laser based sensor may be enhanced by using frequency modulation techniques. As the laser is slowly scanned across a transition, it is also modulated at a higher frequency (f) and detection is done at higher harmonics of the frequency (e.g., 2f). This is done so that i) low frequency drifts in laser intensity do not affect the absorption measurements and ii) excess laser noise, which varies as 1/f, is reduced thereby enhancing the signal-to-noise ratio. These techniques are characterized as either Frequency Modulation (FM) or Wavelength Modulation Spectroscopy (WMS), based on the frequency at which the laser is modulated. Specifically, FM spectroscopy is when the laser is modulated at frequencies greater than the absorption line-width, while WMS is when the modulation frequencies are lower than the absorption line-width. See, J. Reid and D Labrie, "Second-Harmonic Detection with Tunable Diode Lasers—Comparison of Experiment and Theory," *Appl. Phys. B* 26, 203-210 (1981) and an article by the present inventor, G. N. Rao along with C. Gudipaty and D. Martin, "Higher Harmonic Detection Employing Wavelength Modulation Spectroscopy and Near Infra-Red Diode Lasers: An Undergraduate Experiment," *Am. J. Phys.* 77, 821-825 (2009).

SUMMARY OF THE INVENTION

The present invention is directed to improving the accuracy of the detection of trace gas species by conducting wavelength modulation spectroscopy and integrating the absolute value of the recorded spectra across multiple lines of the species. This technique enhances the sensitivity of detection by several orders of magnitude (in favorable cases) compared to a single line wavelength modulation spectroscopy that is conventionally employed for these measurements. Multiple line wavelength modulation spectroscopy can be conducted using a tunable laser and tuning it across several absorption features of the species of interest. The transmitted laser beam which is detected will have the signature features of the trace species.

In the present invention, the laser is modulated with a sinusoidal frequency of tens of kilohertz which is less than the line width of the $NO_2$ transitions, which are of the order of ~900 MHz (0.03 $cm^{-1}$) at a pressure of 110 mbar.

The modulated laser frequency may be expressed as:

$$\nu(t) = \bar{\nu} + a\cos(\omega t); \quad (3)$$

where $\bar{\nu}$ is the mean laser frequency as it is slowly scanned, $a$ is the amplitude of the modulation, and $\omega$ is the angular frequency of the modulation. If the tuning range and modulation amplitude $a$ are small, then the incident laser intensity $I_o(\nu)$ may be treated as constant (this is typically the case for tunable diode lasers as well as the external cavity quantum cascade laser used with the present invention). As a result, equation (2) may be rewritten as:

$$I(\nu) = I_0(\nu)[1 - \alpha(\bar{\nu} + a\cos\omega t)L]. \quad (4)$$

The time dependent term above can be expanded as a cosine Fourier Series:

$$\alpha(\bar{\nu} + a\cos\omega t) = \sum_{n=0} H_n(\bar{\nu})\cos n\omega t, \quad (5)$$

where $\bar{\nu}$ is considered to be constant over a modulation period. $H_n(\bar{\nu})$ is the nth Fourier component of the modulated absorption coefficient. Using a lock-in amplifier (i.e., a phase-sensitive amplifier or detector that can extract a signal with a known carrier wave frequency from an extremely noisy environment) one can detect the nth harmonic of the modulation frequency. This provides a means to measure the absorption since the processed signal of the nth harmonic is proportional to $I_0 H_n(\bar{\nu})L$, where $H_n(\bar{\nu})$ itself is proportional to the absorption coefficient $\alpha$. If the modulation amplitude $a$ is small enough, the nth Fourier Amplitude is proportional to the nth derivative of the absorption signal (See the Reid article):

$$H_n(\bar{\nu}) = \frac{2^{n-1}}{n!} a^n \frac{d^n \alpha(\nu)}{d\nu^n}\bigg|_{\nu=\bar{\nu}} \quad (6)$$

When using WMS, the sensitivity of a spectrometer is often determined by taking the ratio of the peak-to-peak amplitude of the WMS signal of an absorption line to that of the noise level.

Using an absorption line's amplitude to detect a species, however, neglects the width of the line and as a result gives the same intensity for both broad and narrow lines with the same amplitude. For example, even though a 25 ppm sample of $NO_2$ at 600 mbar has twelve times more molecules than the same sample at 50 mbar, its absorption spectrum shows only about a 25% enhancement in peak absorption: The majority of additional absorption manifests itself in the broadening of the lines. See, J. M. Hollas, *High Resolution Spectroscopy*, Second Edition, (Wiley 1998) and an article by the present inventor, A. Karpf and G. N. Rao, "Enhanced Sensitivity for the Detection of Trace Gases Using Multiple Line Integrated Absorption Spectroscopy," *Appl. Opt.* 48, 5061-5066 (2009). The subject matter of the inventor's article is disclosed in his co-pending U.S. patent application Ser. No. 12/878,553 filed on Sep. 9, 2010, and which is incorporated herein in its entirety. As a result, when dealing with broadened lines a more accurate measure of the absorption intensity can be achieved by integrating over the absorption line. Assuming that the absorbance $a=\alpha(\nu)L$ is small (as is typically the case with trace gas detection), the integrated absorption may be written as:

$$S = \int \alpha(\nu) L d\nu \quad (7)$$

Since the absorption coefficient $\alpha(\nu) = \sigma(\nu)N$, where $\sigma(\nu)$ is the cross-section and N is the concentration, the integrated absorption signal for a single line is proportional to the concentration of the species. Based on this, it has been shown that the sum of the areas of a set of absorption lines varies linearly with the concentration, and conducting trace gas detection by integrating multiple absorption lines can enhance the sensitivity of a detector by over one order of magnitude See the inventor's co-pending U.S. patent application Ser. No. 12/878,553 filed on Sep. 9, 2010.

This concept may be extended to further enhance the sensitivity of a detector by integrating the absolute value of the wavelength modulation spectra of a species over multiple lines. Since the nth Fourier amplitude $H_n(\bar{\nu})$ is proportional to the absorption coefficient $\alpha$, integrating the absolute value of the WMS signal yields a result which is also proportional to the concentration. Thus integrating the absolute value of the WMS signal over multiple lines for a species yields a sensitivity comparable to using standard absorption or WMS techniques over many absorption lines, often hundreds of them. If the target species has a dense set of rotational-vibrational states (e.g., $NO_2$), the multiple-line integrated signal could contain the contribution of dozens or even hundreds of lines. Multiple line integrated spectroscopy has the added advantage that saturation and line broadening effects can be minimized compared to long path absorption and WMS techniques.

It should be noted that higher harmonic detection involves higher order derivatives of the absorption lines. See the inventor's article, G. N. Rao, et al. "Higher Harmonic Detection Employing Wavelength Modulation Spectroscopy and Near Infra-Red Diode Lasers: An Undergraduate Experiment," *Am. J. Phys.* 77, 821-825 (2009), which is incorporated herein by reference in its entirety. The absorption lines may be represented by Voigt profiles resulting in derivatives that have both positive and negative parts. When integrating, the contributions from the positive and negative parts effectively cancel. However, since the absolute value of the nth Fourier amplitude is proportional to the concentration, the absolute value of both parts of the signal can be summed over all of the absorption features.

Figure 1:
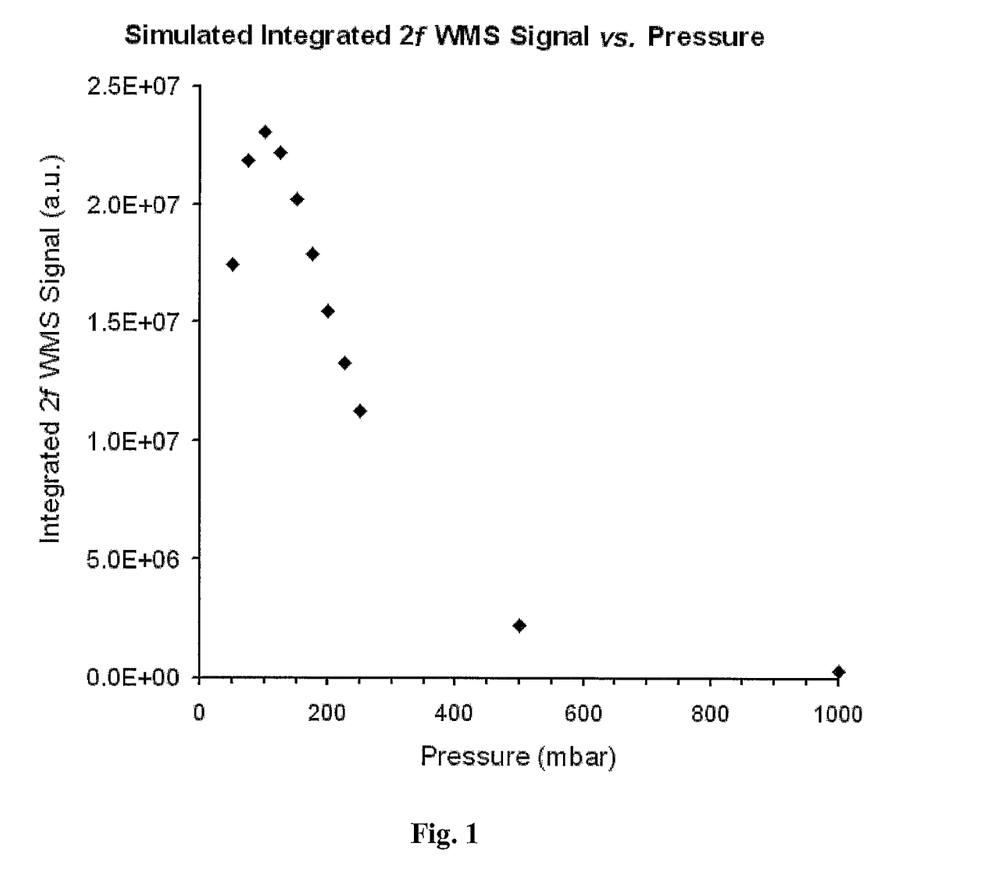
FIG. 1 is a plot of the integrated 2$^{nd}$ harmonic (2f) Wavelength Modulation Spectra vs. pressure generated from simulated spectra based on the HITRAN database.

The integrated WMS signal for a particular concentration may be maximized by preparing the sample at an optimal pressure. The optimal pressure for laser absorption techniques such as Tunable Diode Laser Absorption Spectroscopy (TDLAS) is in the 10-50 mbar range which provides the best balance between sensitivity and selectivity. The multiple-line integrated absorption signal is enhanced by preparing the samples at a higher-pressure (e.g., 600 mbar). This is because pressure-broadening increases the area enclosed by the absorption lines. As seen from Eq. (6), however, the WMS signals are proportional to the derivatives of the absorption lines. As a result, pressure-broadened absorption lines will have shallower slopes, and thus weaker WMS signals. The optimal pressure for an integrated WMS signal is a balance between achieving the steep slopes seen in absorption lines at low pressures, and the increased number of molecules present at higher pressures. This is determined for $NO_2$ by generating a simulated absorption spectrum for several different pressures, taking the $2^{nd}$ derivative of the simulation, and then integrating the results across a desired spectral range (in this case over the peak of the $NO_2$ R-band described below). The amplitude of the integrated signal vs. pressure was plotted (see FIG. 1), and the optimal pressure determined to be approximately 100 mbar. The simulation was generated using the HITRAN database as described by L. S. Rothman, et al., "The HITRAN 2004 molecular spectroscopic database", *J. Quant. Spectrosc. Radiat. Transfer,* 96 139-204 (2005) and the SPECTRA software disclosed by Mikhailenko, et al., "Information-calculating system Spectroscopy of Atmospheric Gases, the structure and main functions," *Atmos. Oceanic Opt.* 18, 685-695 (2005), both of which are incorporated herein by reference in their entirety.

The area under the WMS signals may be enhanced by using a large modulation amplitude a. It has been shown that the peak-to-peak amplitude of a 2nd harmonic WMS signal is maximized when the modulation amplitude $a=2.2\Delta v$, where $\Delta v$=is the Half-Width at Half-Maximum for the corresponding absorption line. See the Reid article. At larger modulation amplitudes, the peak-to-peak amplitude of a 2nd harmonic WMS signal slowly decreases (for a Voigt line profile, it reduces to 80% of its peak value at $a=5\Delta v$). However, at large modulation amplitudes, there is an associated increase in the line width, leading to a broadening of the WMS signal. See, G. Hancock, et al. "Direct and wavelength modulation spectroscopy using a cw external cavity quantum cascade laser," *Appl. Phys. Lett.* 94, 201110; DOI:10.1063/1.3141521 (2009). This broadening leads to a larger integrated area of the absolute value of the $2^{nd}$ harmonic WMS signal.

In the case of large modulation amplitudes, when the laser is modulated using injection current tuning (as is case with tunable diode lasers as well as the quantum cascade laser used in the present invention), the incident laser intensity $I_o(v)$ can no longer be treated as constant. The laser's intensity as well as its frequency will be simultaneously modulated. Eq. (3) may be re-written to take this into account:

$$v(t) = \bar{v} + a\cos(\omega t + \psi); \quad (8)$$

where $\psi$ is the phase shift between the intensity modulation (IM) and the frequency modulation (FM). G. Schilt et al., "Wavelength Modulation Spectroscopy: combined frequency and intensity modulation," *Appl. Opt.* 42, 6728-6738 (2003). The resulting laser intensity may be written as:

$$I_0(t) = \bar{I}_0[1 + i_0\cos(\omega t + \psi_1) + i_2\cos(2\omega t + \psi_2)]; \quad (9)$$

where $\bar{I}_0$ is the average laser intensity at $\bar{v}$, the first cosine term is the first harmonic (1f) term, $i_0$ is the linear (1f) intensity modulation amplitude, $\psi_1$ is the FM/IM phase shift, the second cosine term is the second harmonic (2f) term, $i_2$ is the nonlinear (2f) intensity modulation amplitude (both $i_0$ and $i_2$ are normalized by $\bar{I}_0$), and $\psi_2$ is the phase shift of the nonlinear IM. See H. Li, et al., "Extension of wavelength modulation depth for diode laser absorption measurements in high-pressure gases," *App. Opt.* 45, 1052-1061 (2006).

For the larger tuning and modulation amplitudes involved, Eq. (2) must be rewritten to include contributions from multiple lines:

$$I(v) = I_0(v)[1 - \alpha(v)L] = I_0(v)\left[1 - P\chi_i L\sum_j S_j\varphi_j\right]; \quad (10)$$

where P is the total gas pressure (in atmospheres), $\chi_i$ is the mole fraction of the ith absorbing species (there is an implied summation over the i component species in the case of multiple species in a gas sample), $S_j$ and $\phi_j$ are respectively the line strength and line shape of the jth feature. The summation takes into account the overlap of adjacent features. When modulated, the spectral absorbance $\alpha(\bar{v}+a\cos\omega t)$ may still be expanded as a Fourier series:

$$-\alpha(\bar{v} + a\cos\omega t) = \sum_{n=0}^{\infty} H_n(\bar{v}, a)\cos n\omega t, \quad (11)$$

where the nth Fourier component of the modulated absorption coefficient is:

$$H_n(\bar{v}, a) = -\frac{P\chi_i L}{2\pi}\int_{-\pi}^{\pi}\sum_j S_j\varphi_j(\bar{v} + a\cos\theta)\cos k\theta d\theta \quad (12)$$

As in the case with small modulation amplitude, $H_n$ is proportional to concentration. Li et al. show that the X and Y components of the lock-in signal for 2f detection are:

$$X_{2f} = \frac{G\bar{I}_0}{2}\left[H_2 + \frac{i_0}{2}(H_1 + H_3)\cos\psi_1 + i_2\left(1 + H_0 + \frac{H_4}{2}\right)\cos\psi_2\right] \quad (13)$$

$$Y_{2f} = -\frac{G\bar{I}_0}{2}\left[\frac{i_0}{2}(H_1 - H_3)\sin\psi_1 + i_2\left(1 + H_0 - \frac{H_4}{2}\right)\sin\psi_2\right] \quad (14)$$

The absolute magnitude of the 2f signal is:

$$R_{2f} = \sqrt{X_{2f}^2 + Y_{2f}^2}; \quad (15)$$

If the laser tuning and modulation parameters are kept the same between successive scans of different concentrations of a species, then since the $H_n$ are proportional to the sample concentration, so is the recorded 2f signal from the lock-in amplifier. This in turn means that the signal recorded by integrating the absolute value of the wavelength modulation spectra of a species over multiple lines using large modulation amplitudes will be proportional to the concentration of the target species.

The integrated $2^{nd}$ harmonic WMS signal $W_T$ is defined as a new parameter and it is measured for different concentrations of the target species. As a result, by using pre-calibrated reference mixtures of the desired gas, a $W_T$ vs. concentration curve can be defined that characterizes a particular apparatus according to the invention (e.g., this would take into account the optical path length L, the tuning range, modulation amplitude and other equipment-related factors). The unknown concentrations of the species can then be identified by recording their $W_T$ and identifying their corresponding positions on this curve.

Monitoring trace gases in the atmosphere is a complex process because they often depend on local industrial, environmental, meteorological and other conditions. The constituents of the local atmosphere must be carefully studied for any contributions from other trace gases to the absorption spectra. The possible contributions from other trace species may be addressed either by choosing an appropriate spectral region for the absorption measurements (as described for the detection of $NO_2$ below), or by subtracting their corresponding contribution.

Integrating the wavelength modulated spectra across multiple lines enhances the sensitivity of detection in two ways. The first enhancement is due to the summing of the area under the absolute value of the WMS signal recorded for many spectral lines (which would boost the magnitude of the recorded signal). The second enhancement is from the fact that the integration has the effect of averaging the random components of the noise. Due to the fact that these data are acquired in a single scan, this effective averaging of the noise occurs in a much shorter time span compared to adding the data of repeated scans. The data acquisition rates for multiple line integrated spectroscopy are significantly less than the multiple scans and summation procedures often employed for trace gas detection. See the inventor's co-pending U.S. patent application Ser. No. 12/878,553. This is an advantage for real-time applications in the study of chemical reactions in the atmosphere, breath analysis and detection of explosive compounds. This procedure is particularly valuable for molecules which have a large number of transitions grouped together.

Thus, the present invention is a new technique for the detection of trace species with high sensitivity and selectivity. This method is based on the enhanced sensitivity of detection achieved by employing wavelength modulation spectroscopy and integrating the absolute value of the recorded spectra across multiple absorption lines or overtones of the species. In this technique, the laser is tuned over many rotational vibrational levels (or overtones or simply absorption features) of the trace species and the integrated absolute values of the wavelength modulation spectroscopy is used for sensitive detection instead of a single absorption feature traditionally employed in these measurements. Employing several absorption features or overtones, as many as hundreds of them in favorable cases, enhances the sensitivity of detection by several orders of magnitude. The species could be molecular species, explosive compounds, steroids, and drugs. This technique can be employed with any tunable laser such as diode lasers and quantum cascade lasers with and without an external cavity, optical parametric oscillators, ion, solid state, and dye lasers. The new technique is demonstrated using a continuously tunable external cavity CW quantum cascade laser to record the second harmonic wavelength modulated spectra of $NO_2$ across the peak of the R-branch from 1629.5 cm$^{-1}$ to 1633.9 cm$^{-1}$. By integrating the absolute value of the wavelength modulated spectra, the detection sensitivity of $NO_2$ is improved by a factor of 40 compared to the sensitivity achieved using single line wavelength modulation spectroscopy with the same apparatus.

BRIEF DESCRIPTION OF THE DRAWINGS

The foregoing and other features of the present invention will be more readily apparent from the following detailed description and drawings of an illustrative embodiment of the invention in which.

DESCRIPTION OF AN ILLUSTRATIVE EMBODIMENT OF THE INVENTION

Figure 2:
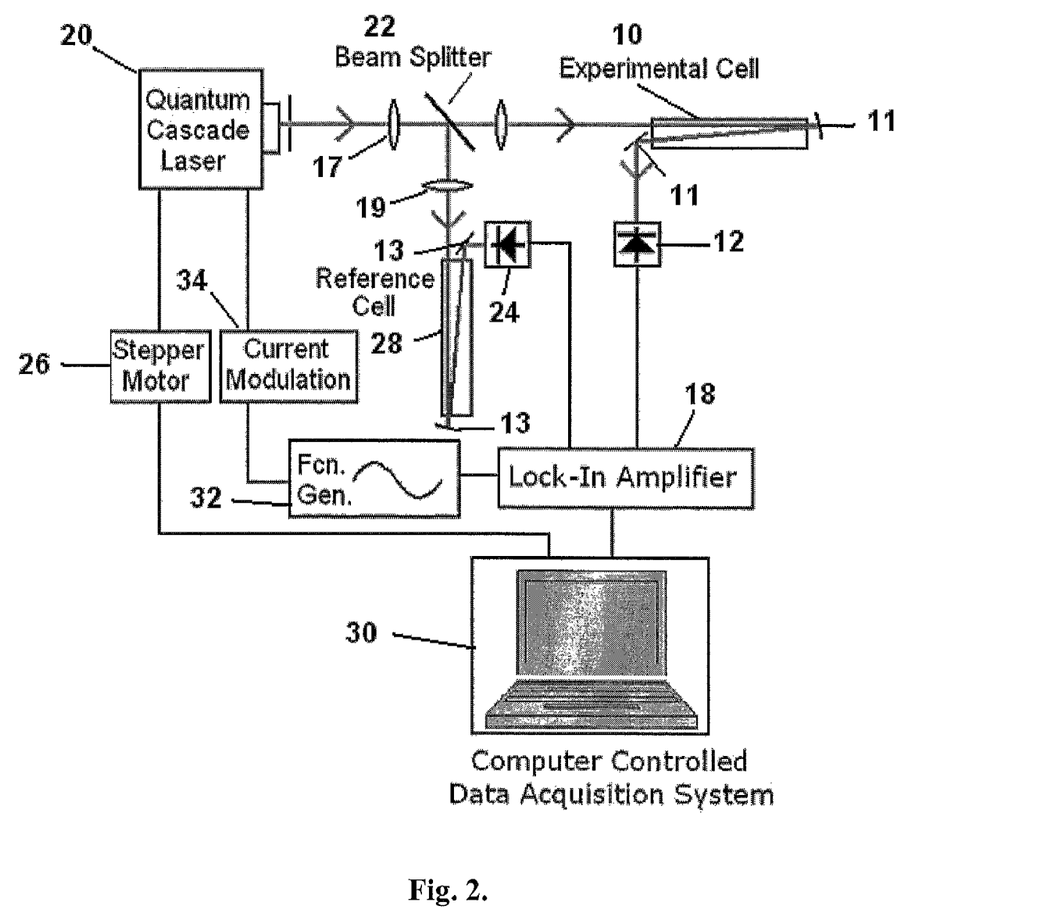
FIG. 2 is a block diagram of the wavelength modulation spectroscopy apparatus of the present invention.

According to the present invention, Wavelength Modulation Spectroscopy of $NO_2$, is carried out using a short-path absorption cell 10 (1 m) as shown in FIG. 2. FIG. 2 shows a Quantum Cascade laser 20 which has a continuous output. The Quantum Cascade Laser source is available from Daylight Solutions (Model TLS-CW-MHF) and has a tuning range of 1601.3 cm$^{-1}$ to 1670 cm$^{-1}$. The laser has an external cavity of the Littrow configuration, which allows a wide range of mode hop-free tuning, provides a narrow line width (~0.001 cm$^{-1}$), and is thus well suited for spectroscopic measurements.

The light pass from laser 20 passes through a first lens 17 of a beam expander and is then incident on a beam splitter 22. One part of the beam is reflected downwardly in the figure to a second lens 19 of a beam expander formed by lenses 17, 19. The other part of the beam travels through the beam splitter and enters cell 10 after passing through the second lens of the beam expander. Two, rectangular, flat, protected gold mirrors 11 are aligned to reflect the beam back and forth seven times through the cell creating a multi-pass cell that increased the path-length to 2.0 m. Upon leaving the cell the light is directed to a photodetector 12. This photodetector may be a two-stage, TE-cooled, IR photovoltaic detector (e.g., the PVI-2TE-8 manufactured by Vigo), which can be operated in a room-temperature environment. The detectors in this equipment may be optically immersed in a high refractive index, hyperhemispherical lens that is part of the detector package.

The output of detector 12 is applied to a Lock-In amplifier 18 for phase sensitive detection, i.e., it can detect the signals at the modulation frequency or its harmonics. This is done so as to improve the signal-to-noise ratio. The lock-in amplifier 18 may be e.g., a Stanford Research Systems SR830 DSP). The output of the Lock-in amplifier is applied to computer 30. In the other beam path, the light exiting the beam expander lens 19 is applied to a reference cell 28. The light that passes through the reference cell 28 is picked up by detector 24 as a reference signal and is applied to Lock-In Amplifier 18. In amplifier 18 the absorption signal from the light that bounced back and forth in the cell 10 has the reference signal subtracted from it and the result is stored in computer 18. The signals from the sample cell and reference cell are subtracted during data processing in the computer 30. The signals from the detectors or lock-in amplifier are fed to the computer 30 using a National Instruments (model PCI-6040E) data acquisition board. A virtual instrument constructed using LabView for Windows was used to record the data in the computer.

The signal is recorded as the stepper motor 26 rotates the external cavity grating of the quantum cascade laser to tune the laser over the desired frequency. The laser tuning is monitored using an etalon [not shown in FIG. 2] and the display screen of the laser controller, as well as by comparing recorded spectra with line positions identified in the HITRAN database. The system may be set to one of six pre-set tuning rates, the slowest of which was 3.125 cm$^{-1}$/sec (the tuning rate employed for recording the NO$_2$ spectra).

The sum of the absolute values of the wavelength modulation spectroscopy difference signals is an indication of the amount of trace gas in the sample. The great accuracy of the present invention is achieved in part by extending the path length with the multi-pass cell 10 and then summing the absolute values of the wavelength modulation spectroscopy signals covering a large number of chosen transitions of the species.

In order to perform Wavelength Modulation Spectroscopy (WMS), a sinusoidal modulation signal is generated by feeding a 45 kHz, 5 V$_{pp}$ sinewave from a function generator 32 (which may be a Stanford Research Systems DS 345 function generator) to the current modulation input on the laser head. The generator output is directed to a current modulator 34, which is a part of the external cavity tunable quantum cascade laser system. The 5 V$_{pp}$ sinewave (the maximum that may be used with the Daylight Solutions QCL) current modulator, corresponds to a modulation amplitude of a=7$\Delta\bar{v}$ (for NO$_2$ at a pressure of 110 mbar $\Delta v$~0.012 cm$^{-1}$). The effect of modulating the laser using a function generator is that the signal signature specific to the species can be detected at the modulation frequency or its harmonics with better signal to noise ratio. The lock-in amplifier 18 is phase locked to the function generator and the signal is detected at the fundamental or harmonics of the modulation frequency which is set on the function generator 32. As a result, the lock-in amplifier can be set to only processes the signals at the appropriate frequency (i.e., the frequency set by the function generator), thus improving the signal-to-noise ratio.

The external cavity tunable quantum cascade laser power output varies as a function of tuning (wavelength), with a minimum output power of 14 mW at 1601.3 cm$^{-1}$, and a maximum of 21 mW at 1640.4 cm$^{-1}$. The output power at 1630 cm$^{-1}$ (the frequency at which wavelength modulation spectroscopy is conducted) was 19.5 mW. The minimum spot size of the beam is approximately 2 mm. Broad range tuning is achieved entirely by rotating the external cavity grating via a stepper motor 26; no current or temperature tuning was necessary.

To measure the sensitivity of detection employing multiple line integrated wavelength modulation spectroscopy, the cell 10 was filled with different concentrations of NO$_2$ (5 ppm, 2.5 ppm, 1 ppm, 0.5 ppm and 0.25 ppm). The NO$_2$ mixtures may be prepared by loading the cell 10 with a pre-calibrated mixture of NO$_2$ in Zero Air (a mix of 20.9% O$_2$ and 79.1% N$_2$). The pre-calibrated NO$_2$ mixture may have a concentration of 5 ppm and the concentration of NO$_2$ is certified by the manufacturer to ±10% of the specified concentration or better. Other concentrations used in the test may be created by loading the cell with the 5 ppm mixture to a certain pressure, and then adding Zero Air to increase the pressure to the desired final value (110 mbar). For example, the 1 ppm concentration is generated by first loading the experimental cell with 22±2 mbar of the pre-calibrated 5 ppm mix of NO$_2$ before additional Zero Air is added to reach a final pressure of 110±10 mbar. Due to limitations in the accuracy of the vacuum/mixing apparatus, the concentrations prepared are accurate to ±15% (e.g., the 1 ppm concentration mixture is expected to contain between 0.85 and 1.15 ppm NO$_2$). The mixing apparatus was tested by generating several concentrations of NO$_2$, and comparing the recorded absorption line intensities with the calculated intensities based on HITRAN data base. This confirmed that the mixtures were within the expected uncertainty.

Tests in the mid and far-infrared regions typically suffer from significant etalon effects. Etaloning in the signal was identified as being due to the beam splitter. The etalon effects from the beam splitter were removed by placing it between the lenses 17, 19 of 2× beam expander (f$_1$=25.8 mm, f$_2$=50.6 mm); the short focal lengths were necessary to create enough divergence to remove the etalon peaks. Wedge windows (AR coated ZnSe with faces that were 1° away from parallel) were used in the cell 10 to remove etalonning that occurs with standard, parallel faced windows. The quantum cascade laser itself exhibited etalonning due to its anti-reflection coatings. This etalonning was compensated for by subtracting empty-cell scans of the laser (which characterized the tuning characteristics of the laser including etalonning) from scans of the cell loaded with NO$_2$.

In order to integrate the recorded spectra for multiple lines over a desired range of frequencies, the laser source must tune without mode hops across that range. The quantum cascade laser used with the present invention is capable of mode hop-free tuning between 1603.5 cm$^{-1}$ and 1670 cm$^{-1}$. This provides access to half of the NO$_2$ P-branch and the entire NO$_2$ R-branch (the peak absorption in the R-branch occurs at 1630.3 cm$^{-1}$). The next consideration was to select a region with a strong dense spectrum, and free from interference due to other species. A review of the component species present in the atmosphere and the species included in the HITRAN database showed that only H$_2$O and NH$_3$ have transitions in the region of interest that were potentially strong enough to cause interference. See the Rothman article and National Aeronautic and Space Administration, "Earth Fact Sheet—Terrestrial Atmosphere," http://nssdc.gsfc.nasa.gov/planetary/factsheet/earthfact.html. However the effects of NH$_3$ can be ignored due to the fact that the expected concentration of NH$_3$ in ambient air (away from significant forest, industry or farm sources) is in the 100 ppt-10 ppb range, and the fact that the NH$_3$ transitions are over two orders of magnitude weaker than the corresponding NO$_2$ transitions. The strength of the water lines, however, necessitated the selection of a region in which they did not significantly interfere with recording NO$_2$ spectra.

Figure 3A:
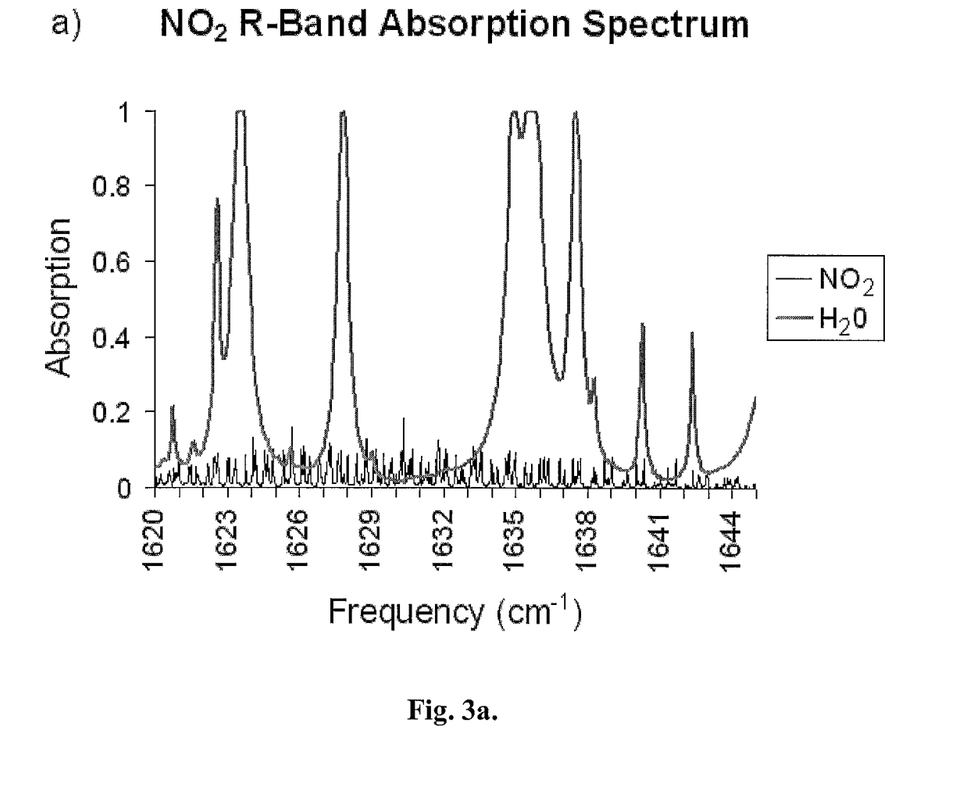
FIG. 3a shows a simulated $NO_2$ spectrum (50 ppm at 200 mbar) illustrating the regions where water lines overlap.

FIG. 3a shows a simulated NO$_2$ spectrum (50 ppm at 200 mbar) for the R-branch between 1620 cm$^{-1}$ and 1645 cm$^{-1}$ illustrating the regions where the water lines (due to ambient water vapor in the beam path leading to the cell) overlap and thus overwhelm any potential signal from the NO$_2$ R-branch. This simulation was generated using the HITRAN database and the SPECTRA software developed by Mikhailenko, et al. This does not directly account for water vapor continuum absorption effects; but, the effect of the continuum on the WMS signals, which are derivatives of the absorption data, is believed to be small. This is corroborated by the fact that the line positions and line intensities calculated using the HITRAN data agreed well with the reported experimental results. The strength of the water lines was selected to match typical conditions in the mid-latitude U.S. during the summer months (the water vapor density used was 14.97 g/m$^3$ which corresponds to a relative humidity of 71% at 23° C., and is the average humidity in Washington, D.C. in July). It can be seen in FIG. 3 that the region between the water lines at 1627.82

Figure 3B:
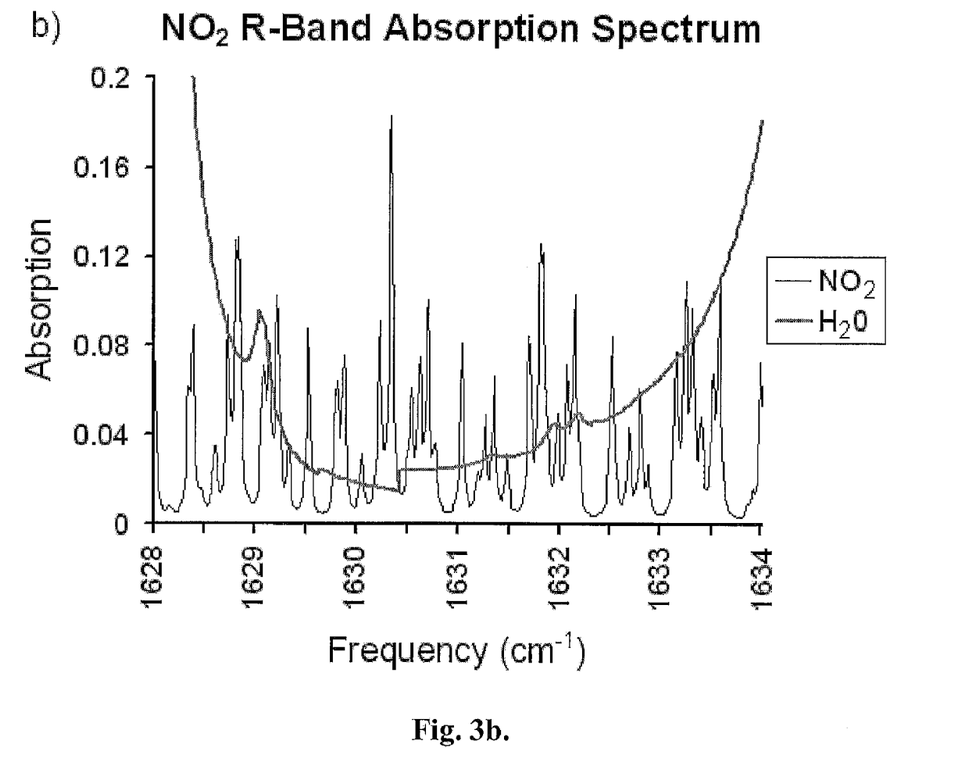
FIG. 3b is a close-up of the region shown in FIG. 3a where the spectrum is recorded and integrated.

$cm^{-1}$ and 1634.97 $cm^{-1}$ proves to be the longest continuous region in which absorption due to the water lines does not overwhelm the $NO_2$ lines, and covers the peak of the R-branch. This region of the spectrum is used because it has a strong dense $NO_2$ spectrum that is free from interference due to water lines. FIG. 3b shows a close-up of the region that was recorded and integrated.

Due to the broad width of the water lines and limitations in the apparatus, the ability to record continuous $2^{nd}$ harmonic WMS $NO_2$ signals is limited to the region between 1629.5 $cm^{-1}$ and 1633.9 $cm^{-1}$. It is important to note that this tuning range covers over 400 $NO_2$ transitions, of which approximately 20% may be considered relatively strong (i.e., having transition strengths over 10% that of the strongest transition in the R-branch). It should also be noted that the strength and width of the water lines in the simulation were calibrated to match the apparatus (which had a roughly 1 meter path from the laser to the experimental cell).

The sensitivity of the apparatus is determined using Wavelength Modulation Spectroscopy of a single absorption feature by recording the $2^{nd}$ harmonic WMS of the $NO_2$ doublet at 1631.02 $cm^{-1}$ (at a pressure of 110±10 mbar and concentration of 2.5 ppm). This feature is selected because it is both a typically strong feature in the R-band (intensity $\sim 10^{-19}$ cm/molecule), and is relatively well separated from neighboring absorption features. The doublet results from the transitions between the (0 0 1)-(19 2 17) and (0 0 0)-(18 2 16) levels; the individual lines are located at 1631.023 $cm^{-1}$ and 1631.026 $cm^{-1}$ (note that the $(v_1\ v_3\ v_3)$-$(N\ K_a\ K_c)$ level notation is used). The separation of the lines of 0.003 $cm^{-1}$ is narrower than the 0.023 $cm^{-1}$ full width at half maximum ("FWHM") of the individual lines at 110 mbar, and results in a single observed absorption feature.

Figure 4A:
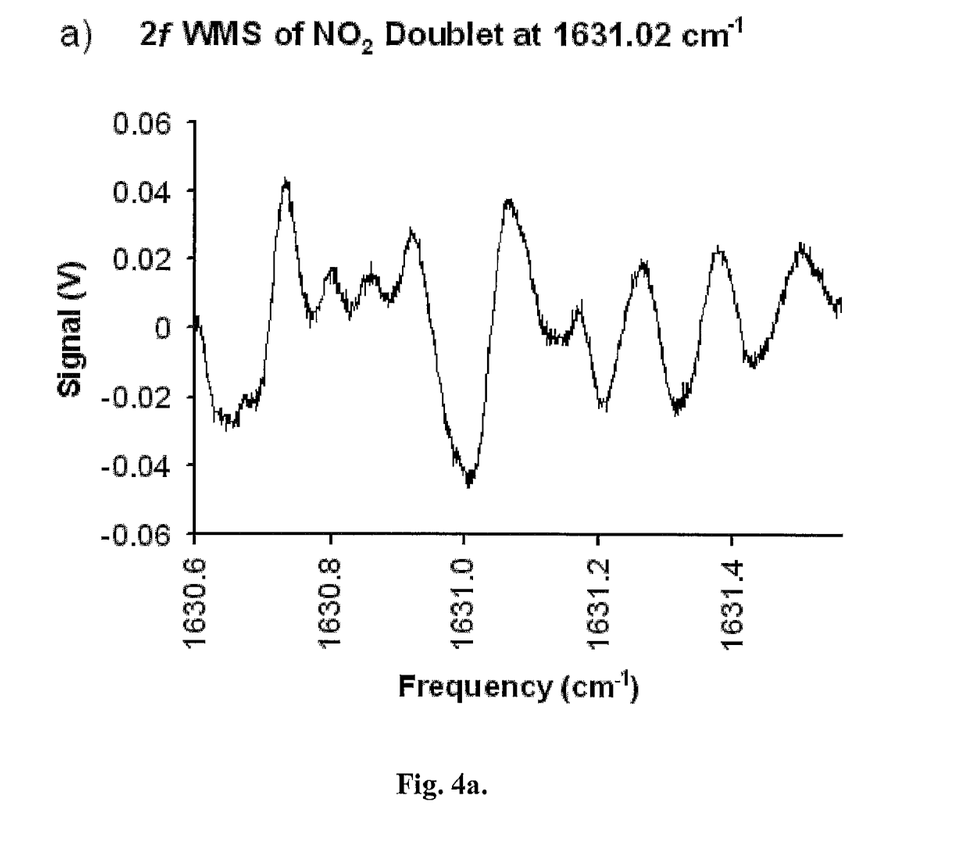
FIG. 4a is a graph of the second harmonic WMS signal of the absorption spectrum of the doublet at 1629.52 cm$^{-1}$.
Figure 4B:
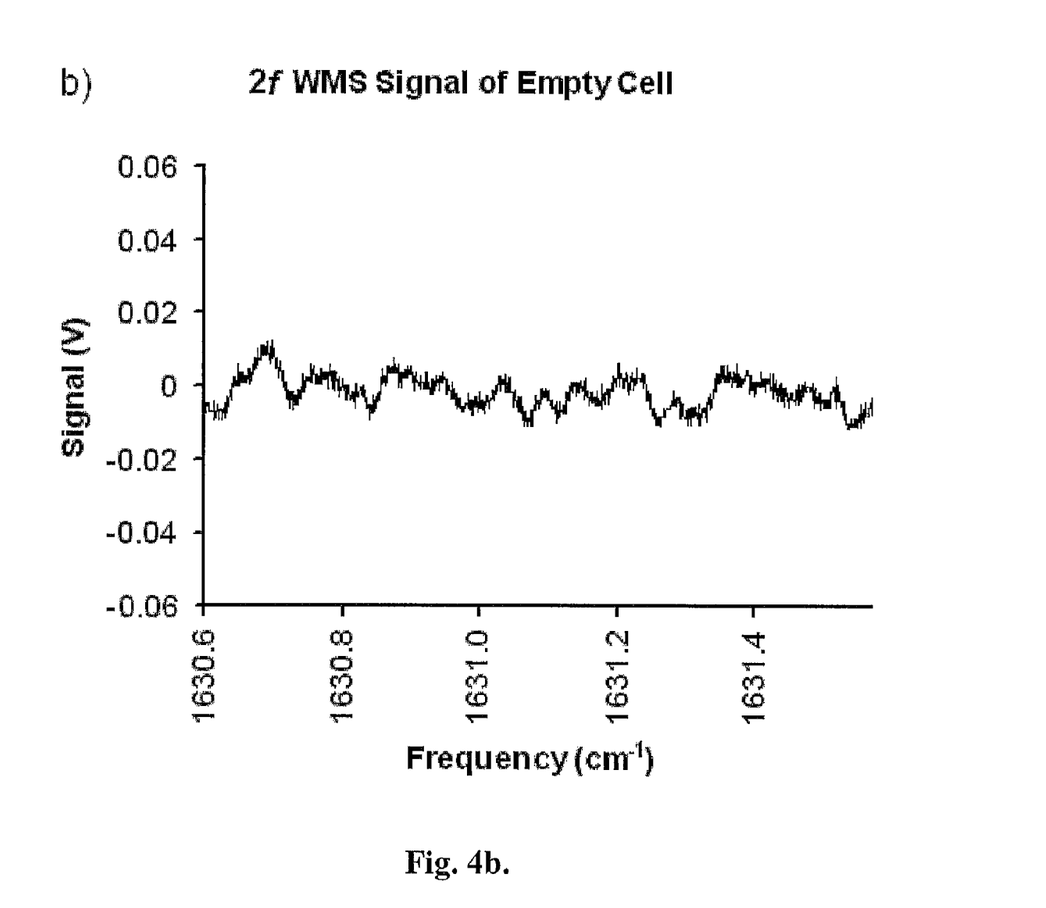
FIG. 4b is an illustration of noise content for the same region shown in FIG. 4a and which was obtained under the same operating conditions, but with an empty cell.

The recorded $2^{nd}$ harmonic WMS spectrum is shown in FIG. 4a. It is the absorption spectrum of the doublet at 1629.52 $cm^{-1}$. The $NO_2$ concentration was 2.5±0.38 ppm at a pressure of 110±10 mbar. Note that the $2^{nd}$ harmonic signals from other nearby multiplets can be seen at 1630.8 $cm^{-1}$ and in the region above 1631.2 $cm^{-1}$. The amplitude of the $2^{nd}$ harmonic WMS from the 1631.02 doublet is compared to the noise spectrum seen in FIG. 4b (which was obtained under the same operating conditions, but with an empty cell). Based on this comparison it can be seen that the signal-to-noise (S/N) ratio for the doublet is approximately 10. The sensitivity of the apparatus determined using the second harmonic WMS signal from a single absorption feature is therefore approximately 250 ppb.

Figure 5A:
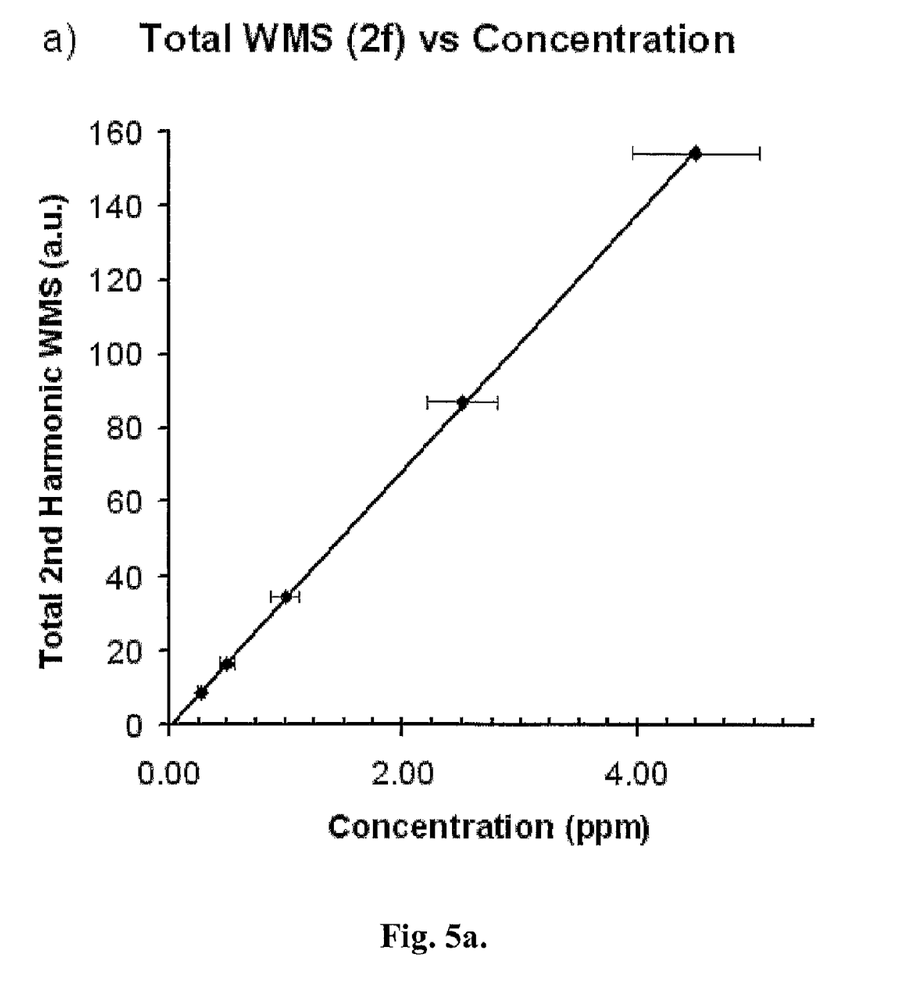
FIG. 5a is a plot of the total 2$^{nd}$ harmonic WMS signal vs. concentration.
Figure 5B:
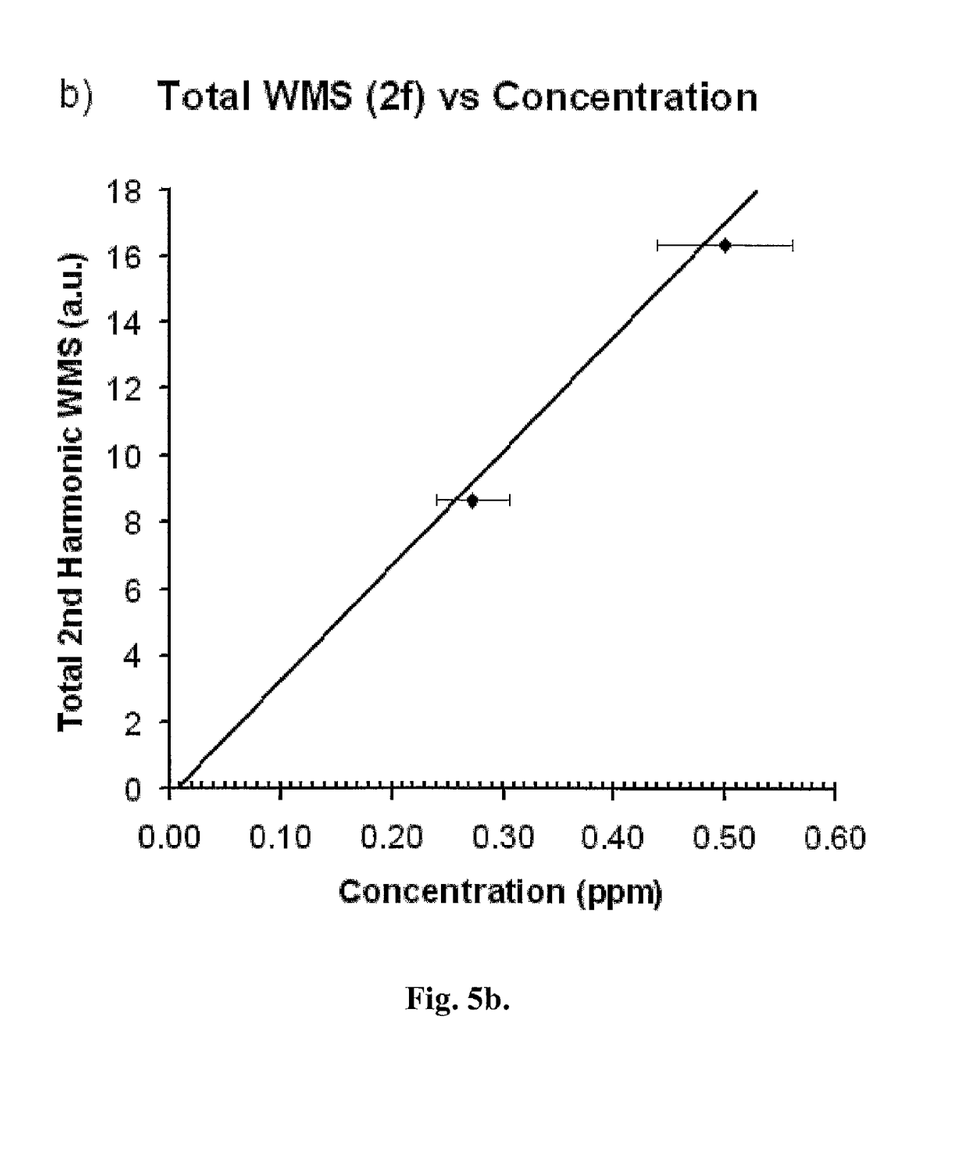
FIG. 5b is an expanded scale of the low concentration region of the plot of FIG. 5a showing the low concentration data points.

To measure the sensitivity that can be obtained by integrating the multi-line wavelength modulation spectra recorded over a tuning range, the second harmonic WMS spectra is recorded for five concentrations of $NO_2$ (4.5 ppm, 2.5 ppm, 1 ppm, 0.5 ppm, and 0.27 ppm), at a pressure of 110±10 mbar. The spectra are recorded in the frequency range 1629.5 $cm^{-1}$ to 1633.9 $cm^{-1}$. The concentrations were selected to ensure that the data were in the weakly absorbing regime (i.e., the absorption of the strongest line was less than 5%). The absolute values of the data obtained for each concentration are then summed to yield the integrated $2^{nd}$ harmonic WMS signal $W_T$ for the corresponding concentration. Each of these values is subtracted from the integrated $2^{nd}$ harmonic WMS signal recorded for an evacuated sample cell. This results in the determination of the area under the absolute value of the WMS spectrum for the corresponding concentration (i.e., the total 2nd harmonic WMS signal for a given concentration). FIG. 5a shows a plot of the total $2^{nd}$ harmonic WMS signal vs. concentration, as well as a weighted linear least-squares fit of these data (the y-axis is given in arbitrary units). The linear relationship between the integrated $2^{nd}$ harmonic WMS signal of the various concentrations is clearly seen. The y-intercept is used to determine the sensitivity of detection. FIG. 5b uses an expanded scale to display the low concentration portion of the data.

The instrument's sensitivity is determined from the y-intercept of the linear fit. The y-intercept value of −0.2025 total $2^{nd}$ harmonic WMS units is divided by the slope of the fit (34.46 total $2^{nd}$ harmonic WMS units/ppm) to obtain a sensitivity on the order of 6 ppb. This shows a factor of 40 improvement in sensitivity for the multiple line integrated wavelength modulation spectroscopy compared to wavelength modulation spectroscopy of a single line conducted using the same apparatus. It should also be noted that this shows a factor of 20 improvement in sensitivity over that disclosed in the inventor's co-pending U.S. patent application Ser. No. 12/878,553 filed on Sep. 9, 2010 using multiple line integrated absorption spectroscopy.

Even though the $NO_2$ mixtures were generated using Zero-Air (a dehumidified air mixture), the results are representative of what one would expect if the $NO_2$ was in ambient air. This is a result of the apparatus layout, where the laser beam travels through approximately 1 meter of ambient air before reaching the cell. In fact, it should be noted that the multiple line integrated WMS technique is less susceptible to interference from water lines compared to other absorption-based techniques. This is due to the fact that achieving sensitivities on the ppb-level using a single line requires long path lengths (10's or 100's of meters), resulting in a saturation and broadening of the water lines present in the sample, which can prevent the observation of $NO_2$ spectra unless one first takes preparatory steps such as dehumidifying the sample.

The technique of the present invention enhances the sensitivity of a spectrometer for trace gas detection by integrating the absolute value of the wavelength modulation spectra from multiple spectral lines. In particular, wavelength modulation spectroscopy of a single line is used with a tunable, CW quantum cascade laser, and a short-path absorption cell to detect low concentrations of $NO_2$ with a sensitivity of approximately 250 ppb. By integrating the $2^{nd}$ harmonic WMS spectra over multiple lines with the same apparatus, it can detect concentrations of $NO_2$ with a sensitivity on the order of 6 ppb, demonstrating a factor of 40 improvement in the instrument's sensitivity. This technique can be applied for the detection of several trace species such as trace gases, explosive compounds, steroids etc. However, it should be noted that multiple line integrated wavelength modulation spectroscopy is particularly valuable for the high sensitivity detection of polyatomic species such as $NO_2$ that have dense rotational-vibrational spectra over a relatively compact frequency range. Though this embodiment was described with a quantum cascade laser with a wide mode hop-free tuning range, the invention can be employed with any tunable laser source, such as a diode laser, that is capable of tuning across multiple transitions of the target species. Additional improvements to the sensitivity may be achieved by using this technique with long optical path-length apparatus such as a Herriot cell or ICOS, and should enable sensitivity in the ppt range.

While the invention has been particularly shown and described with reference to a preferred embodiment thereof, it will be understood by those skilled in the art that various changes in form and details may be made therein without departing from the spirit and scope of the invention.

I claim:

1. A method for detecting trace gases using absorption spectroscopy, comprising the steps of:
providing a laser beam that can be tuned over a frequency range covering more than one absorption line or feature of the target species;
modulating the laser frequency;
directing the laser beam through a medium containing the trace gas;
detecting and recording at least one harmonic of the modulated laser beam after it emerges from the medium;
tuning the frequency of the laser over a range of interest determined by the absorption spectra or features of the trace gas species; and
integrating by adding the absolute values of the harmonic spectra recorded for multiple lines over the range of frequencies.

2. The method of claim 1 wherein the step of modulating the laser frequency involves providing a varying current to the laser head.

3. The method of claim 2 wherein further including the step of providing a varying current involves providing a sinusoidal wave current to the laser head so as to cover several absorption lines or features of the species.

4. The method of claim 3 including injection current tuning over which the modulating sine wave can be superimposed.

5. The method of claim 1 wherein the gas being detected is $NO_2$.

6. The method of claim 1 further including the steps of:
splitting the laser beam so that part of the light enters the medium and part is reflected to a reference cell that does not contain trace gas;
detecting and recording the higher harmonic of the modulated laser beam after it emerges from the reference cell;
subtracting the recorded reference cell signal from the recorded medium signal to get a difference signal; and
integrating by summing the absolute values of the wavelength modulation spectroscopy difference signals for multiple lines over a desired range of frequencies.

7. The method of claim 1 wherein the step of providing a laser beam involves the steps of:
using a function generator to generate a modulation signal;
employing a current modulator with the modulation signal to produce a modulated current signal; and
applying the modulated current signal to the laser to modulate the laser output.

8. The method of claim 6 wherein a second harmonics of the laser beams from the absorption cell and reference cell are recorded in a lock-in amplifier and the lock-in amplifier is phase locked to the modulation frequency set on function generator.

9. The method of claim 1 wherein the laser is a quantum cascade laser.

10. The method of claim 1 wherein the laser is one of a diode laser and a quantum cascade lasers operated with or without an external cavity configuration.

11. The method of claim 1 wherein the medium is an enclosed cell.

12. The method of claim 11 wherein the enclosed cell is one of a single pass absorption cell, multipass absorption cell (Herriott cell, astigmatic cell); Off-axis integrated cavity and output spectroscopy cell.

13. The method of claim 11 further including the step of providing mirrors on the input and output of the cell arranged so that the laser beam is reflected back and forth through the cell to form a multi-pass cell.

14. The method of claim 1 wherein the trace gas species include automobile exhaust and explosive compounds.

15. Apparatus for detecting trace gases using absorption spectroscopy, comprising:
a laser source that provides a laser output that is tunable over several rotational vibrational bands of the molecular species or several absorption features of the compounds;
a current modulator for modulating the frequency of the laser output;
a medium in which the trace gas species are located and through which the laser output is passed;
a photodetector for detecting a harmonic of the modulated signal frequency after it emerges from the medium and generating a signal related thereto;
a storage medium for storing the detection signals from the photodetector,
a tuner for tuning the laser frequency over a range of frequencies determined by the absorption spectra or features of the trace gas species; and
an integrator for summing the stored detection signals for multiple lines over the range of frequencies and the modulated frequencies.

16. The apparatus of claim 15 wherein the trace gas is $NO_2$.

17. The apparatus of claim 16 wherein the desired range is 1601.3 $cm^{-1}$ to 1670 $cm^{-1}$.

18. The apparatus of claim 15 wherein the laser beam is modulated at a rate is 3.9 kHz.

19. The apparatus of claim 15 wherein the laser source is a quantum cascade laser.

20. The apparatus of claim 15 further including a beam expander after the laser and before the detector to minimize the etalonning effect.

21. The apparatus of claim 15 further comprising:
a beam splitter intercepting a portion of the light pulse before it enters the medium and reflecting part of it in a different direction;
a reference cell without any trace gas species receiving the light reflected by the beam splitter;
second photodetector intercepting the light passing out of the reference cell and generating a signal related to a harmonic thereof;
a storage medium for storing the detection signals from the second photodetector; and
a subtraction circuit for subtracting the second photodetector signal from the photodetector signal; and
an integrator for a summing the difference in the stored detection signals for multiple lines over the desired range of frequencies.

22. The apparatus of claim 21 further including a lock-in amplifier connected to the photodetectors, said lock-in amplifier including the storage medium for the photodetector and second photodetector output, as well as the subtraction circuit.

23. The apparatus of claim 15 wherein the laser source comprises:
a quantum cascade laser;
a function generator to generate a modulation signal;
a current modulator driven with the modulation signal to produce a modulated current signal, said modulated current signal being applied to the head of the laser to modulate the laser light output.

24. The apparatus of claim 23 wherein the lock-in amplifier and the current modulator are phase locked.

25. The apparatus of claim 21 further comprising a beam expander including two lenses interposed between the laser and the medium, and a second beam expander interposed in the reference beam.

26. The apparatus of claim 15 wherein the trace gas species include explosives, drugs and steroids.

27. The apparatus of claim 23 wherein the current modulation signal is a sinusoidal wave.

28. The apparatus of claim 15 wherein the medium is an enclosed cell and further including mirrors on the input and output of the cell arranged so that the beam is reflected back and forth through the cell so that it acts as a multi-pass cell.

* * * * *